United States Patent [19]
Lee et al.

[11] Patent Number: 5,453,505
[45] Date of Patent: Sep. 26, 1995

[54] N-HETEROAROMATIC ION AND IMINIUM ION SUBSTITUTED CYANINE DYES FOR USE AS FLUORESCENCE LABELS

[75] Inventors: Linda G. Lee, Palo Alto; Sam L. Woo, Redwood City, both of Calif.

[73] Assignee: Biometric Imaging, Inc., Mountain View, Calif.

[21] Appl. No.: 268,852

[22] Filed: Jun. 30, 1994

[51] Int. Cl.$^6$ ............... C07D 209/02; C07D 209/56; A61K 47/22
[52] U.S. Cl. ............... 544/124; 435/4; 435/7.8; 435/968; 436/172; 436/542; 436/538; 436/800; 546/273; 548/312.1; 548/427; 548/455; 530/802; 536/24.3; 536/24.31; 536/24.32; 536/25.32
[58] Field of Search ............ 546/273; 530/802; 548/312.1, 427; 544/124; 536/24.3, 24.31, 24.32, 25.32; 435/968, 4, 7.8; 436/538, 542, 172, 800

[56] References Cited

U.S. PATENT DOCUMENTS

| | | | |
|---|---|---|---|
| 2,526,632 | 10/1950 | Brooker et al. | 548/312.1 X |
| 2,704,755 | 3/1955 | Kendall et al. | 548/312.1 X |
| 2,856,404 | 10/1958 | Brooker et al. | 548/312.1 X |
| 2,954,292 | 9/1960 | Duffin et al. | 546/273 X |
| 2,965,485 | 12/1960 | Duffin et al. | 546/273 X |
| 3,194,805 | 7/1965 | Brooker et al. | 548/312.1 X |
| 3,359,113 | 12/1967 | Depoorter et al. | 548/312.1 X |
| 3,541,089 | 11/1970 | Heseltine et al. | 546/273 X |
| 3,558,614 | 1/1971 | Jenkins | 548/312.1 X |
| 3,560,102 | 5/1972 | Riester | 548/312.1 X |
| 3,576,639 | 4/1971 | Jenkins | 548/312.1 X |
| 3,580,911 | 5/1971 | Mee et al. | 546/273 |
| 3,586,672 | 6/1971 | Litzerman | 546/273 X |
| 4,366,314 | 12/1982 | Beecken | 546/273 X |
| 5,268,486 | 12/1993 | Waggoner et al. | 548/427 |

FOREIGN PATENT DOCUMENTS

| | | | |
|---|---|---|---|
| 0296873 | 12/1988 | European Pat. Off. | 546/273 |
| 0944027 | 6/1956 | Germany | 546/273 |

OTHER PUBLICATIONS

Mujumdar, et al., "Cyanine Dye Labeling Reagents: Sulfoindocyanine Succinimidyl Esters", Bioconjugate Chemistry (1993), vol. 4, pp. 105–111.

Oi, et al., "Fluorescent Phycobiliprotein Conjugates for Analyses of Cells and Molecules", The Journal of Cell Biology (1982), vol. 93, pp. 981–986.

Coons, et al., "Localization of Antigen in Tissue Cells", Journal of Exp. Med. (1950), vol. 91, pp. 1–13.

Primary Examiner—Floyd D. Higel
Attorney, Agent, or Firm—Haynes & Davis

[57] ABSTRACT

The present invention relates to iminium ion substituted cyanine dyes having a fluoresence absorbance of between about 500 and 900 nm, a reduced tendency to aggregate and enhanced photostability. The cyanine dyes of the present invention are represented by the formula

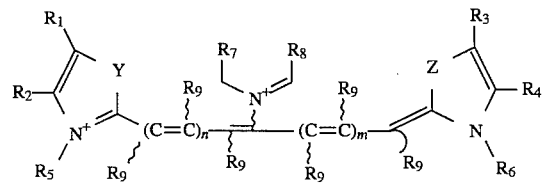

wherein n is 0, 1, 2 or 3;

m is 0, 1, 2 or 3;

$R_1$ and $R_2$ are taken together to form an aromatic ring or a fused polycyclic aromatic ring;

$R_3$ and $R_4$ are taken together to form an aromatic ring or a fused polycyclic aromatic ring;

$R_5$ and $R_6$ are independently selected from the group consisting of $(CH_2)_pX$ where p is 1–18 and X is a functional group that reacts with amino, hydroxyl and sulfhydryl nucleophiles;

$R_7$ and $R_8$ are independently selected from the group consisting of hydrogen, C1–C10 alkyl groups and where $R_7$ and $R_8$ are taken together to form a five- or six- membered heterocyclic ring;

$R_9$ are each independently selected from the group consisting of hydrogen, alkyl and where more than one $R_9$ are taken together to form a five- or six- membered ring;

Y is selected from the group consisting of $C(CH_3)_2$, S, O and Se; and

Z is selected from the group consisting of $C(CH_3)_2$, S, O and Se.

36 Claims, 4 Drawing Sheets

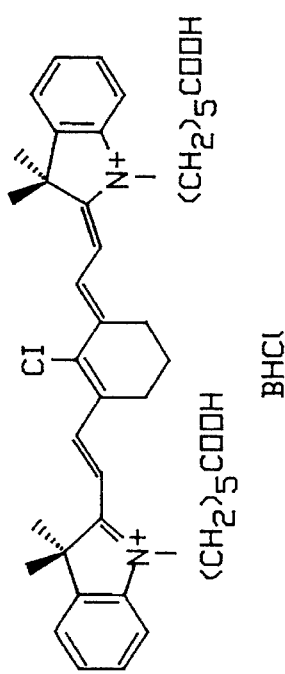
FIG.2A
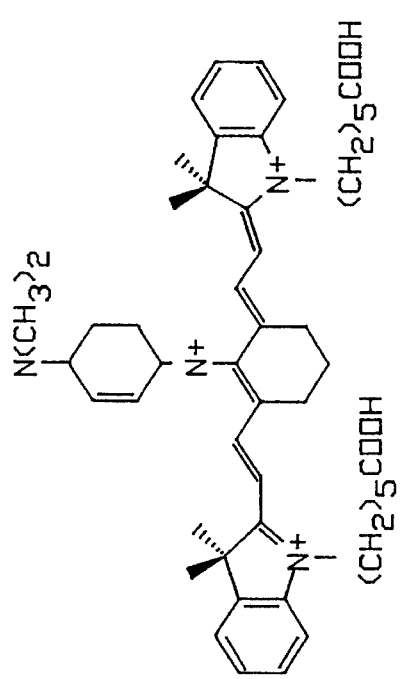
FIG.2B
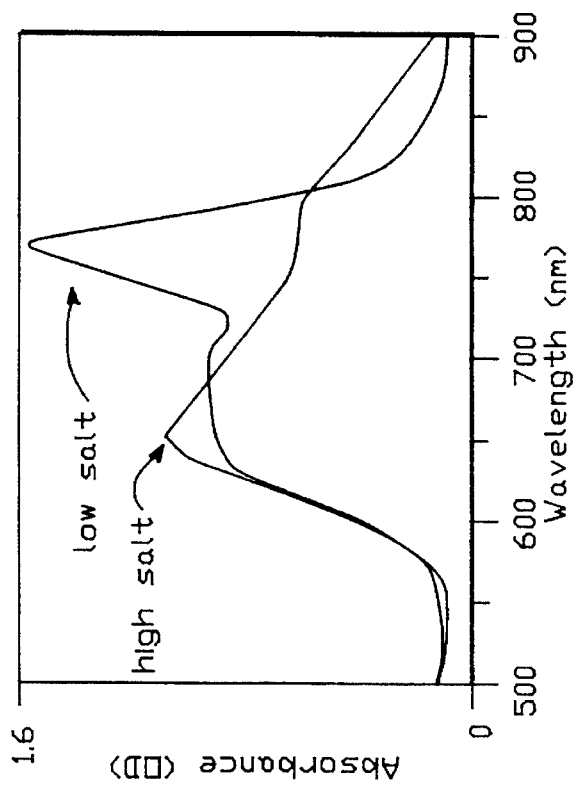
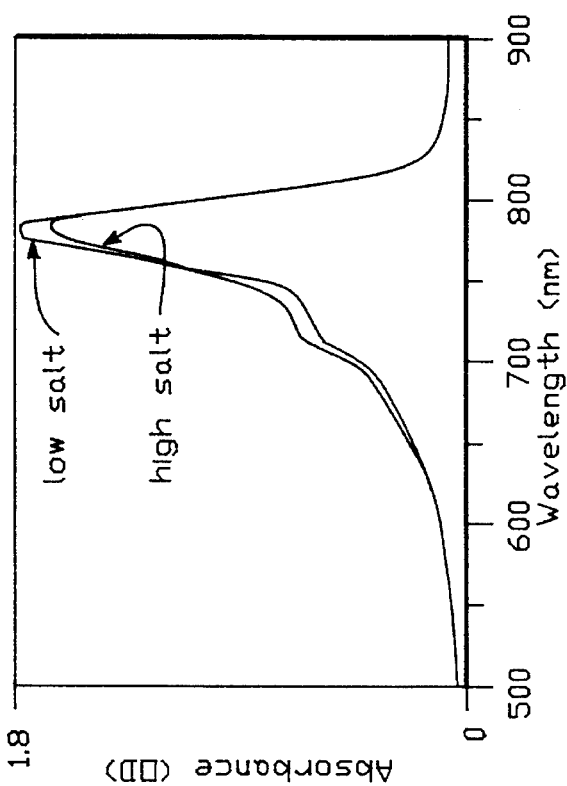

N-HETEROAROMATIC ION AND IMINIUM ION SUBSTITUTED CYANINE DYES FOR USE AS FLUORESCENCE LABELS

FIELD OF THE INVENTION

The present invention relates to cyanine dyes for use as fluorescent probes. More specifically, the present invention relates to cyanine dyes substituted with either an N-heteroaromatic ion or an iminium ion, the ion reducing the aggregation of the cyanine dyes and enhancing the photostability of the dyes.

BACKGROUND OF THE INVENTION

Fluorescent dyes have a wide variety of uses including the labeling of antibodies, DNA, carbohydrates and cells. In order for a fluorescent dye to function as a label, the dye must bind to the molecule or cell to be labeled. Fluorescent labels are therefore designed to include at least one reactive moiety which reacts with amino, hydroxyl and/or sulfhydryl nucleophiles present on the molecules being labeled. Examples of suitable reactive moieties include carboxylic acids, acid halides, sulfonic acids, esters, aldehydes, disulfides, isothiocyanates, isocyanates, monochlorotriazine, dichlorotriazine, mono- or di-halogen substituted pyridines, mono- or di-halogen substituted diazines, maleimide, aziridines, sulfonyl halides, hydroxysuccinimide esters, hydroxysulfosuccinimide esters, imido esters, hydrazines, azidonitrophenyl, azides, 3-(2-pyridyl dithio)-propionamide and glyoxal. Additional suitable reactive moieties for use in fluorescent labels are described in U.S. Pat. No. 5,268,486 which is incorporated herein by reference.

Fluorescent dyes commonly have an absorbance range of between about 300 and 900 nm and preferably have a Stokes shift of at least about 20 nm. Fluorescent dyes that absorb in the 500 to 900 nm range are preferred because they are spectrally removed from other components that may be present in a biological sample and because they may be used with inexpensive light sources. Fluorescent dyes that have a high extinction coefficient and a high quantum yield are also preferred.

Fluorescent dyes used for labeling biomolecules, such as carbohydrates, proteins and DNA, are preferably water soluble since the biomolecules to be labeled generally have limited solubility in nonaqueous solvents. It is known to increase the water solubility of a dye by adding hydrophilic groups such as sulfonate groups and hydroxyl groups. Examples of water soluble dyes that may be used as fluorescent probes include fluorescein (Coons, et al., *J. Exp. Med.* (1950) 91 1–13), phycobiliproteins (Oi, et al., *J. Cell. Biol.* (1982) 93 981) and Cy5 (Mujumdar, et al., *Bioconjugate Chem.* (1993) 4 105–111).

It is important that the fluorescent dye is photostable. However, dyes with a fluorescence absorbance greater than 500 nm tend to be less photostabile.

Fluorescent dyes also should not be prone to aggregation. Dye aggregation, also known as "stacking" increases the frequency of fluorescence quenching which reduces the strength of the fluoresence signal observed. Most fluorescent dyes are large planar molecules, are intrinsically hydrophobic and therefore have a tendency to aggregate or "stack," especially in aqueous solutions. Dyes with a fluoresence absorbance greater than 500 nm generally have a greater tendency to stack due to their increased size and associated lower solubility. Non-aggregating, photostable fluorescent dyes with a fluoresence absorbance greater than 500 nm are therefore needed.

Fluorescent probes are particularly prone to stack in high salt solutions and when in high local concentrations on protein surfaces. For example, tetramethylrhodamine, a commonly used laser dye, produces protein-dye conjugates which predominantly consist of the aggregated dye. Aggregated dyes appear blue-shifted by visible absorbance spectra. Amino-substituted cyanine dyes, such as IR144, are prone to aggregation in aqueous solutions, even in low-salt solutions (i.e. 0.1M NaCl). Non-aggregated amino-substituted cyanine dyes have only been found to exist in organic solvents. The absorbance spectra of protein-dye conjugates can be simulated by obtaining spectra of the dye in high salt solutions (e.g. 4M NaCl). Dye aggregation may be minimized by constructing highly ionic dyes such as arylsulfonates taught in U.S. Pat. No. 5,268,486 or by using naturally occurring fluorescent probes such as phycobiliproteins.

SUMMARY OF THE INVENTION

The present invention relates to cyanine dyes substituted with either an N-heteroaromatic ion or an iminium ion which have a fluoresence absorbance of between about 500 and 900 nm, a reduced tendency to aggregate and enhanced photostability. The cyanine dyes of the present invention are represented by the formula

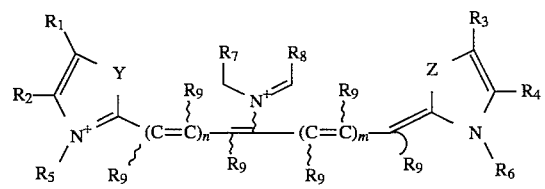

wherein n is 0, 1, 2 or 3;

m is 0, 1, 2 or 3;

$R_1$ and $R_2$ are taken together to form an aromatic ring or a fused polycyclic aromatic ring;

$R_3$ and $R_4$ are taken together to form an aromatic ring or a fused polycyclic aromatic ring;

$R_5$ and $R_6$ are independently selected from the group consisting of $(CH_2)_pX$ where p is 1–18 and X is a functional group that reacts with amino, hydroxyl or sulfhydryl nucleophiles;

$R_7$ and $R_8$ are independently selected from the group consisting of hydrogen, C1–C10 alkyl groups and where $R_7$ and $R_8$ are taken together to form a five- or six- membered heterocyclic ring;

$R_9$ are each independently selected from the group consisting of hydrogen, alkyl and where more than one $R_9$ are taken together to form a five- or six- membered ring;

Y is selected from the group consisting of $C(CH_3)_2$, S, O and Se; and

Z is selected from the group consisting of $C(CH_3)_2$, S, O and Se.

The present invention also relates to a method for using the cyanine dyes of the present invention for fluorescence labeling molecules, particularly biomolecules such as antibodies, DNA, carbohydrates and cells.

BRIEF DESCRIPTION OF THE DRAWINGS

FIG. 2 depicts the spectra of BHCl and BHDMAP in low (0.1M NaCl, 50 mM phosphate, pH 7) and high (3.8M NaCl, 50 mM phosphate, pH 7) salt solutions.

DETAILED DESCRIPTION OF THE INVENTION

Figure 1:
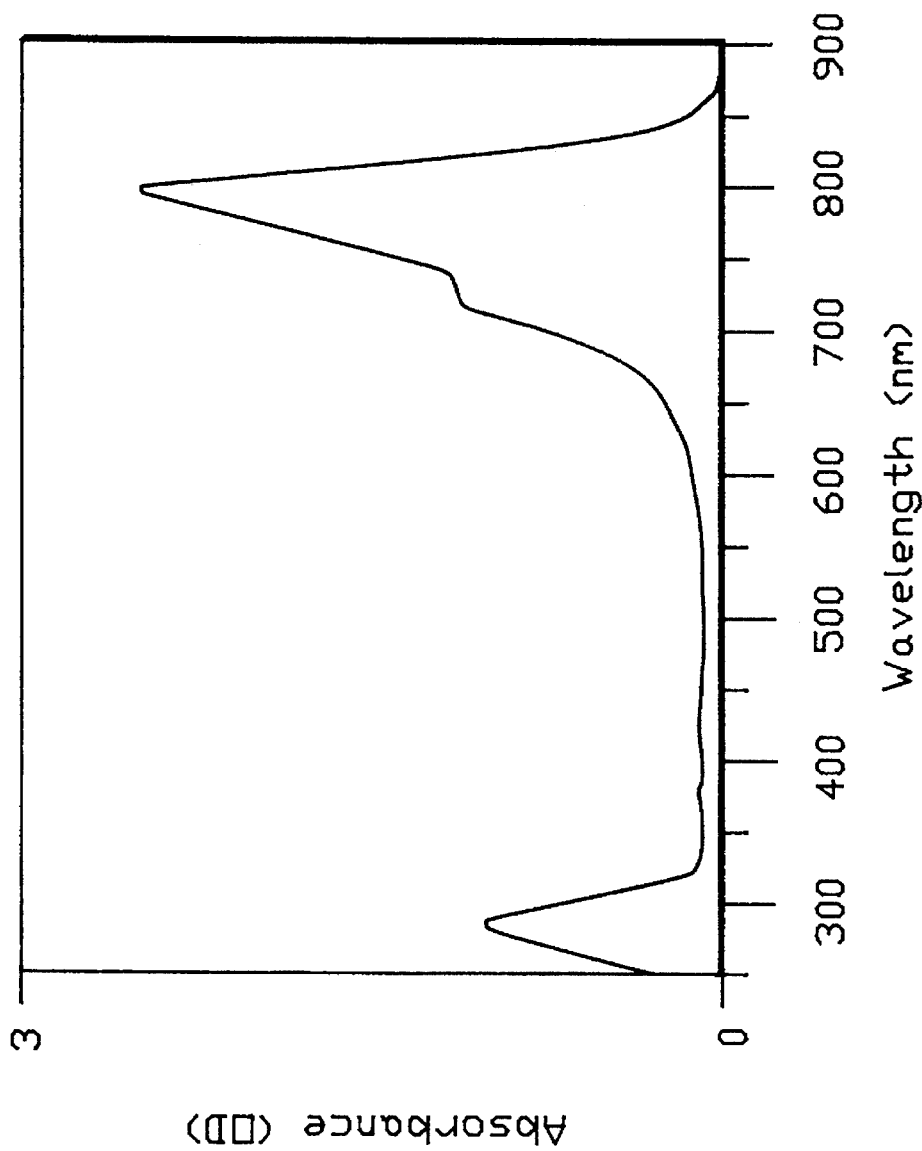
FIG. 1 depicts the absorbance spectrum of a BHDMAP-protein conjugate.

The present invention relates to a class of cyanine dyes substituted with either an N-heteroaromatic ion or an iminium ion having a fluorescence absorbance between about 500 and 900 nm. This class of cyanine dyes have the advantage of being photostable and are not prone to aggregation. The present invention also relates to a method for fluorescence labeling molecules using the substituted cyanine dyes of the present invention as fluorescent probes.

The N-heteroaromatic ion and iminium ion substituted cyanine dyes of the present invention are represented by the formula:

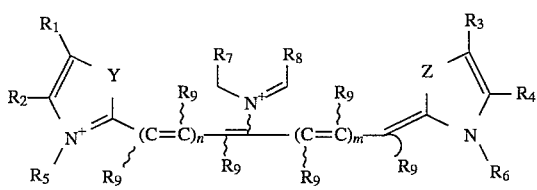

wherein n is 0, 1, 2 or 3;

m is 0, 1, 2 or 3;

$R_1$ and $R_2$ are taken together to form an aromatic ring or a fused polycyclic aromatic ring;

$R_3$ and $R_4$ are taken together to form an aromatic ring or a fused polycyclic aromatic ring;

$R_5$ and $R_6$ are independently selected from the group consisting of $(CH_2)_pX$ where p is 1–18 and X is a functional group that reacts with amino, hydroxyl and sulfhydryl nucleophiles;

$R_7$ and $R_8$ are independently selected from the group consisting of hydrogen, C1–C10 alkyl groups and where $R_7$ and $R_8$ are taken together to form a five- or six- membered heterocyclic ring;

$R_9$ are each independently selected from the group consisting of hydrogen, alkyl and where more than one $R_9$ are taken together to form a five- or six- membered ring;

Y is selected from the group consisting of $C(CH_3)_2$, S, O and Se; and

Z is selected from the group consisting of $C(CH_3)_2$, S, O and Se.

Preferably, (n+m) is less than or equal to 3. Most preferably, n=1 and m=1.

$R_1$–$R_2$ and $R_3$–$R_4$ are both preferably taken together to form a benzene or naphthalene ring. The aromatic ring or fused polycyclic aromatic rings formed by $R_1$ and $R_2$ taken together and $R_3$ and $R_4$ taken together may be either unsubstituted or substituted. Substitution of the aromatic ring or rings with electron donating groups, such as primary, secondary and tertiary alkyl groups, may be used to lower the absorbance wavelength of the dye relative to an unsubstituted dye. Meanwhile, substitution of the aromatic ring or rings with electron withdrawing groups such as nitro, cyanate, acid, halide, alkoxy, aryloxy, ester, ether, sulfide, thioether, alcohol, alkene, alkyne and aryl groups, may be used to increase the absorbance wavelength of the dye relative to an unsubstituted dye.

The reactive moieties (X) employed with $R_5$ and $R_6$ may be any functional group that reacts with the amino, hydroxyl and/or sulfhydryl nucleophiles commonly found on the carbohydrates, proteins, DNA or cells to be labeled by the fluorescent dye. Examples of suitable reactive moieties include, but are not limited to, carboxylic acids, acid halides, sulfonic acids, esters, aldehydes, disulfides, isothiocyanates, isocyanates, monochlorotriazine, dichlorotriazine, mono- or di-halogen substituted pyridines, mono- or di-halogen substituted diazines, maleimide, aziridines, sulfonyl halides, hydroxysuccinimide esters, hydroxysulfosuccinimide esters, imido esters, hydrazines, azidonitrophenyl, azides, 3-(2-pyridyl dithio)-propionamide and glyoxal. Additional suitable reactive moieties for use in fluorescent labels are described in U.S. Pat. No. 5,268,486. The reactive moieties used in $R_5$ and $R_6$ are preferably succidimidyl esters.

$R_7$ and $R_8$ are preferably taken together to form a heterocyclic five- or six- membered ring including, for example, pyridinium, imidazolium, pyrrolium, pyrazolium, pyrazinium, pyrimidinium, pyridazinium, quinolinium, purinium and isoquinolinium. $R_7$ and $R_8$ are more preferably taken together to form a pyridinium or an imidazolium ring. $R_7$ and $R_8$ are most preferably taken together to form a 4-dimethylaminopyridium, 4-(4-morpholinyl) pyridinium, or a 1-methylimidazolium substitutent.

The heterocyclic ring formed by $R_7$ and $R_8$ taken together may be substituted or unsubstituted. $R_7$ and $R_8$ may be further substituted by either electron donating or electron withdrawing groups in electron communication with the aromatic system of the dye in order to influence the fluorescence absorbance wavelength of the dye. Substitution of $R_7$ and $R_8$ with electron donating groups, such as primary, secondary and tertiary alkyl groups, may be used to decrease the fluorescence absorbance wavelength of the dye relative to where $R_7$ and $R_8$ are substituted with hydrogen. Meanwhile, substitution of $R_7$ and $R_8$ with electron withdrawing groups such as nitro, cyanate, acid, halide, alkoxy, aryloxy, ester, ether, sulfide, thioether, alcohol, alkene, alkyne and aryl groups, may be used to increase the fluorescence absorbance wavelength of the dye relative to where $R_7$ and $R_8$ are substituted with hydrogen.

The $R_9$ substituents are preferably selected such that the carbon atoms situated $\alpha$ and $\alpha'$ to the iminium ion form part of either a five- or six- membered ring. The five- or six- membered ring may be substituted or unsubstituted.

Y and Z may be either $C(CH_3)_2$, S, O or Se. Preferably, Y and Z are $C(CH_3)_2$. Y and Z serve to keep the cyanine dye relatively planar and provide the dye with fluorescence.

A preferred subclass of cyanine dyes of the present invention includes those cyanine dyes of the formula

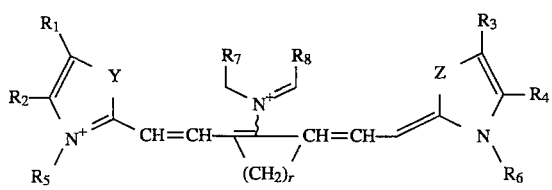

wherein $R_1$, $R_2$, $R_3$, $R_4$, $R_5$, $R_6$, $R_7$, $R_8$, Y and Z are as specified above and wherein r is either 1, 2 or 3.

Table 1 provides the names, structures, absorbance and fluorescence emission wavelengths of several cyanine dyes of the present invention and of their chloro-substituted precursors. NHCl and ZFHCl do not have an absorbance maximum in phosphate buffered saline (PBS).

TABLE 1

Dye Structures and Spectral Data

| Name | Structure | Abs Max in PBS (nm) |
|---|---|---|
| BHCl | 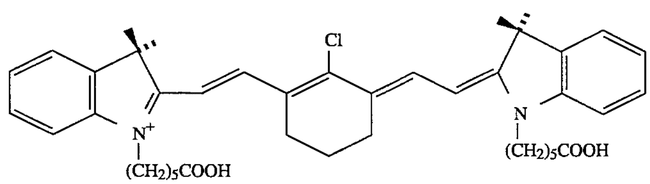 | 776 |
| BHDMAP | 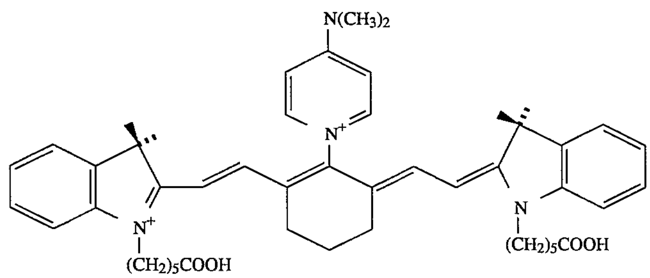 | 786 |
| BHMI | 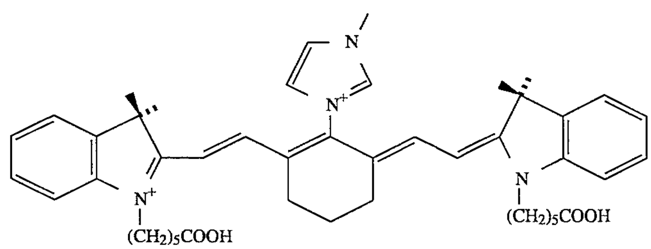 | 792 |
| BHPPY | 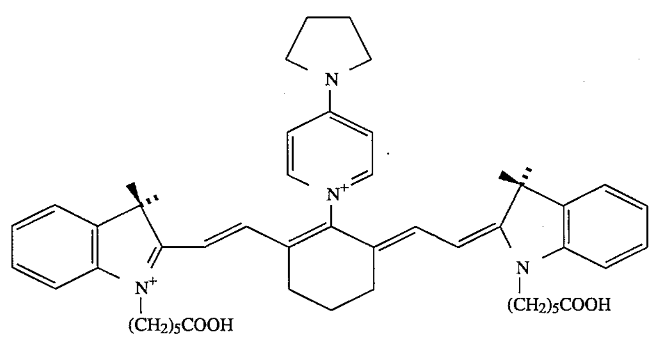 | 786 |

TABLE 1-continued

Dye Structures and Spectral Data

| Name | Structure | Abs Max in PBS (nm) |
|---|---|---|
| BHMPY | 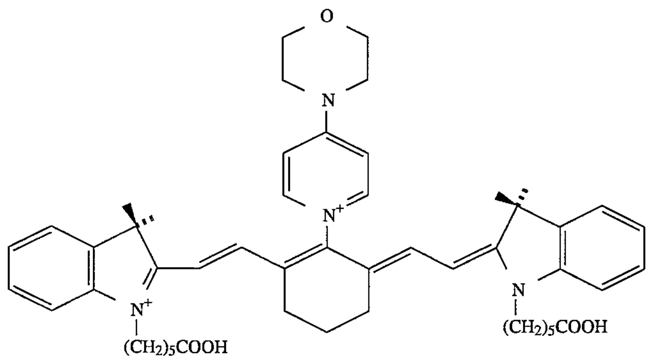 | 786 |
| NHCl | 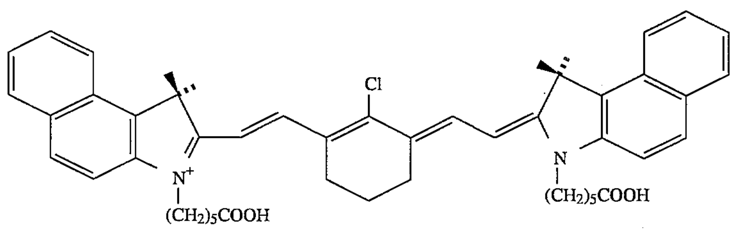 | — |
| NHDMAP | 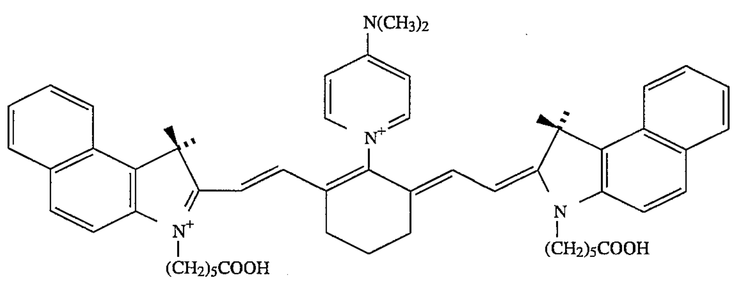 | 825 |
| NHMI | 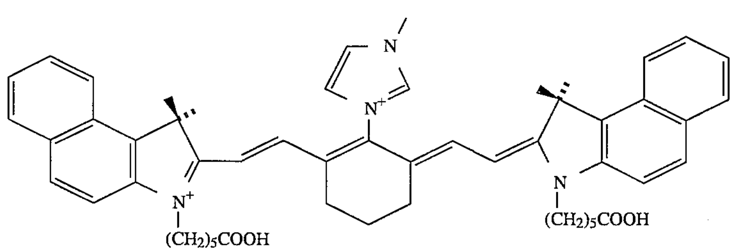 | 832 |
| BPCl | 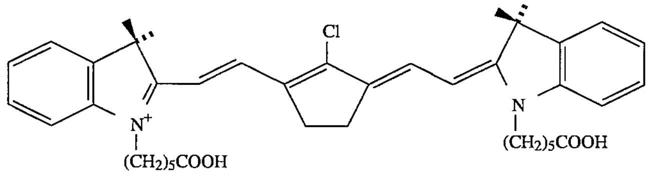 | 798 |

TABLE 1-continued

Dye Structures and Spectral Data

| Name | Structure | Abs Max in PBS (nm) |
|---|---|---|
| BPDMAP | 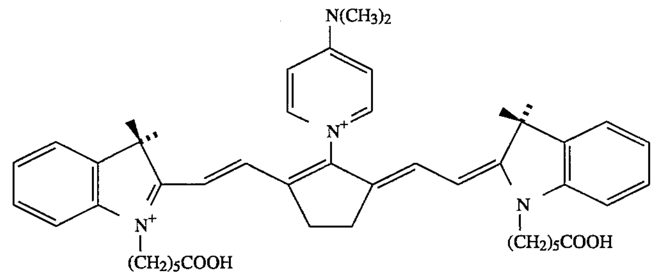 | 816 |
| ZFHCl | 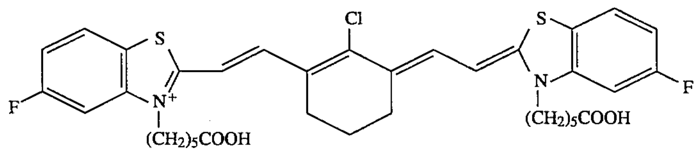 | — |
| ZFHDMAP | 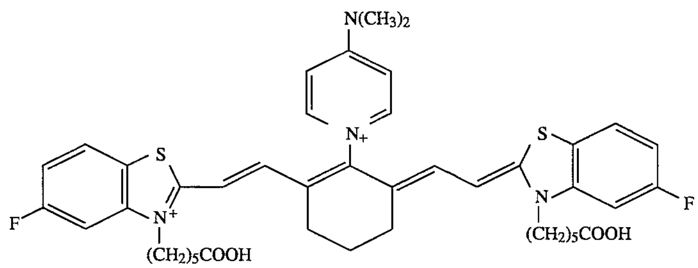 | 803 |

The cyanine dyes of the present invention have been found to possess enhanced photostability and are not prone to aggregation. Without being bound by theory, it is believed that the N-heteroaromatic ion and the iminium ion inhibits aggregation of these dyes. In addition to inhibiting aggregation, the N-heteroaromatic ion and the iminium ion are also believed to contribute to the photostability of these dyes.

The following examples set forth the synthesis and physical characterization of some of the cyanine dyes of the present invention. Further objectives and advantages of the present invention other than those set forth above will become apparent from the examples which are not intended to limit the scope of the present invention.

EXAMPLES

1. Synthesis of BHDMAP

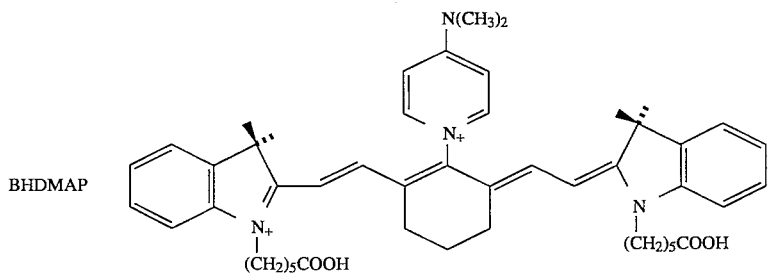

BHDMAP

The stepwise synthesis of BH-DMAP, shown above, is provided in Examples 1(a)–1(d).

1(a). Synthesis of 1-(5'-carbonylpentyl)-2,3,3-trimethylindolinium bromide

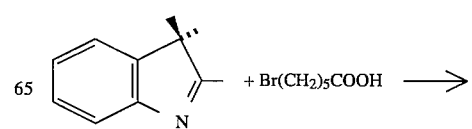

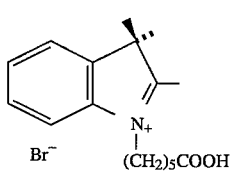

A mixture of 1,3,3-trimethylindoline (3.8 g, 23 mmol) and 6-bromohexanoic acid (4.6 g, 23 mmol) were stirred under nitrogen at 110° C. for 12 h. The red solid was triturated with 2×20 mL refluxing ethyl acetate followed by 20 mL refluxing acetone. The pink powder was filtered and air dried. Yield: 6.3 g, 18 mmol, 77%. $^1$H NMR: (CD$_3$OD) δ1.54 (m, 2H), 1.61 (s, 6H), 1.71 (m, 2H), 2.00 (m, 2H), 2.34 (t,J=7.3Hz, 2H), 4.53 (t, J=7.7Hz, 2H), 7.62–7.9 (m, 4H). The 2-methyl protons are acidic and exchange with the deuterated solvent.

1(b). Synthesis of N-[5-anilino-3-chloro-2,4-(propane-1',3'-diyl)-2,4-pentadien-1-ylidene]-anilinium chloride

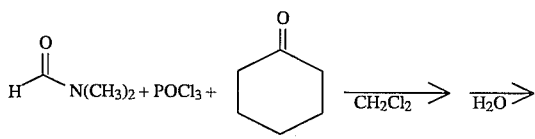

A modification of the procedure taught by Reynolds in Reynolds, et al., *J. Org. Chem.* (1977) 42 885 was used. A solution of dimethylformamide (7.6 g, 100 mmol) and dichloromethane (2 mL) was cooled in ice with stirring under nitrogen. Phosphorus oxychloride (12 g, 75 mmol) in dichloromethane (2 mL) was added dropwise over 10 min. Cyclohexanone (2 g, 20 mmol) in dichloromethane (3 mL) was added dropwise over 10 min. The solution turned yellow. The solution was refluxed for 3 h and became orange.

The solution was poured over 50 g of ice. The organic layer was separated and discarded. Aniline (5 g, 54 mmol) was added. A dark purple precipitate formed immediately. The solid was filtered and washed with 1N HCl and air dried. Yield: 1.9 g, 5.3 mmol, 27%.

1(c). Synthesis of BHCl

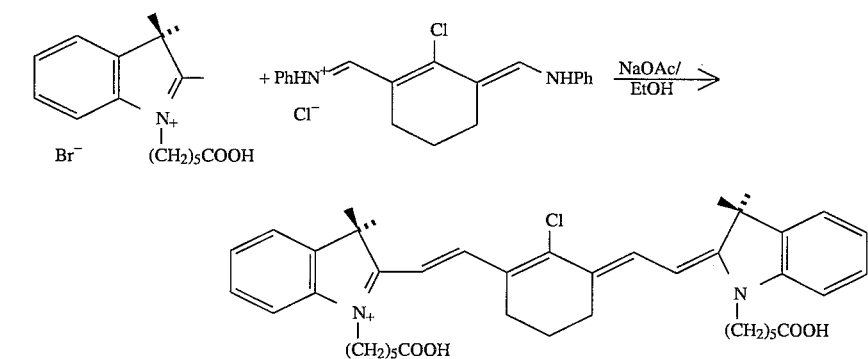

-continued

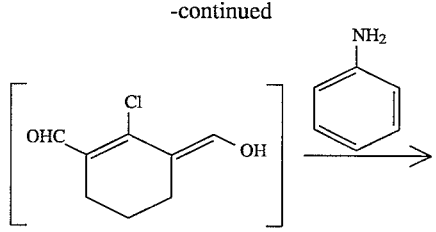

A solution of 1-(5'-carboxypentyl)-2,3,3-trimethylindolinium bromide (100 mg, 0.28 mmol), N-[5-anilino-3-chloro-2,4-(propane-1',3' -diyl)-2,4-pentadien-1-ylidene] anilinium chloride (50 mg, 0.14 mmol), sodium acetate (50 mg, 0.36 mmol) and ethanol (20 mL) was refluxed for 30 min. The solution was concentrated to dryness and the residue was trituated twice with 5 ml of 2N HCl. The residue was dried in vacuo to give a dark oil. Yield: 90mg, 0.12mmol, 43%. $^1$H- NMR (CD$_3$OD) δ 1.51 (m, 4H), 1.7 (m, 4H), 1.74 (s, 12H), 1.87 (m,4H), 1.97 (m, 2H), 2.35 (m, 4H), 2.75 (m, 4H), 4.18 (m, 4H), 7.32 (m, 2H), 7.4–7.55 (m, 8H), 8.45 (m, 2H).

1(d). Synthesis of BHDMAP

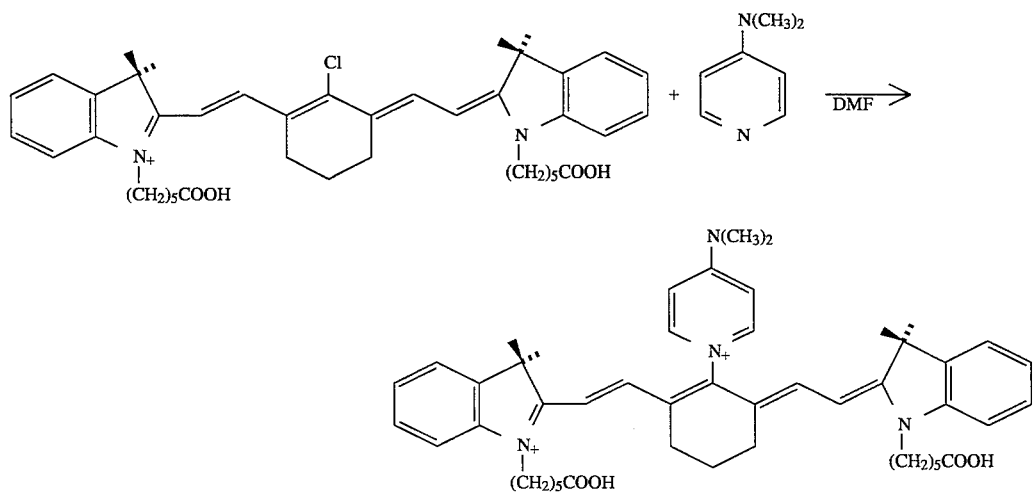

To a solution of BHCl (10 mg, 0.014 mmol) in DMF was added 4-dimethylaminopyridine (8.6 mg, 0.071 mmol). The reaction was monitored by HPLC analysis on a POROS R2 column, 4×100 mm (20% to 80% acetonitrile vs. 0.1M triethylammonium acetate over 4 min, 5 mL/min). After 15 h at ambient temperature, the reaction was complete. The solution was then concentrated to dryness and dissolved in dichloromethane (0.15 mL). Ethyl acetate (1 mL) was added. The dark precipatate was separated by centrifugation. Yield: 11 mg, 0.13 mmol, 93%. $^1$H-NMR(CD$_3$OD): δ1.41 (s, 12H), 1.48 (m, 4H), 1.69 (m, 4H), 1.85 (m, 4H), 2.11 (m, 2H), 2.36 (m, 4H), 2.84 (m, 4H), 3.49 (s, 6H), 4.21 (m, 4H), 6.42 (d, J=11.8Hz, 2H), 6.94 (d, J=11.8Hz, 2H), 7.3–7.5 (m, 10H), 8.30 (d, J=6.7Hz, 2H). Fluorescence emission maximum: 807 nm.

2. Synthesis of NHMI

NHMI

The stepwise synthesis of NHMI, shown above, is provided in Examples 2(a)–2(c).

2(a). Synthesis of 4,5-benzo-1-(5'-carboxypentyl)-2,3,3-trimethylindolinium bromide.

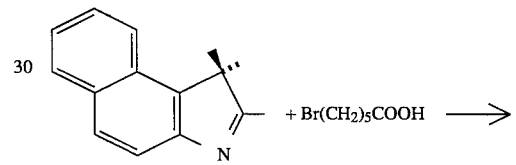

-continued

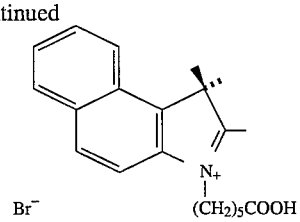

A mixture of 4,5-benzo-2,3,3-trimethylindoline (0.5 g, 2.4 mmol) and 6-bromohexanoic acid (0.5 g, 2.6 mmol) were stirred under nitrogen at 110° C. for 2 h. The black tar was triturated with 20 mL acetone. The gray powder was filtered and air dried. Yield: 0.8 g, 2 mmol, 83%. $^1$H NMR: (CD$_3$OD) δ1.59 (m, 2H), 1.73 (m, 2H), 1.85 (s, 6H), 2.06 (m, 2H), 2.35 (t, J=7.0 Hz, 2H), 4.64 (t, J=7.7 Hz, 2H), 7.7–8.3 (m, 6H). The 2-methyl protons are acidic and exchange with the deuterated solvent.

2(b). Synthesis of NHCl

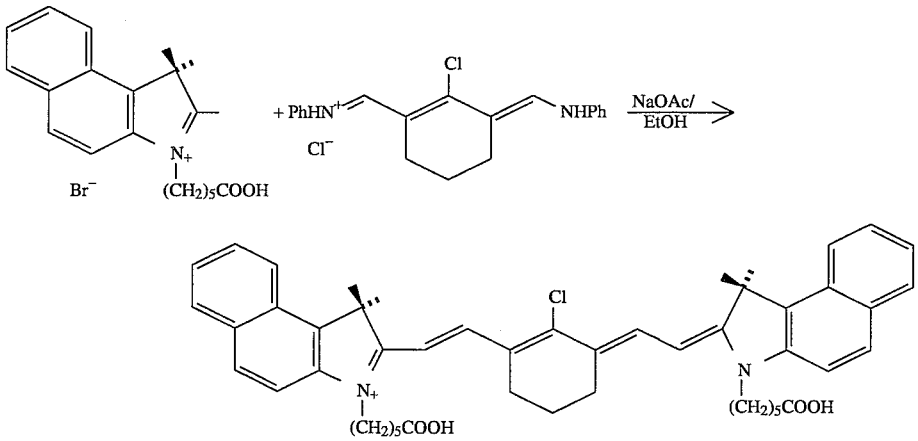

A mixture of 4,5-benzo-1-(5'-carboxypentyl)-2,3,3-trimethylindolinum bromide (110 mg, 0.28 mmol), N-[5-anilino-3-chloro- 2,4-propane-1',3'-diyl)-2,4-pentadien-1-ylidene] anilininum chloride (50 mg, 0.14 mmol) and sodium acetate (100 mg, 0.72 mmol) was dissolved in 20 ml of ethanol. After stirring at room temperature for 15 hours under N$_2$, the solvent was removed under reduced pressure. The residue was triturated with a 1:1 solution of ethyl acetate and hexane (100 ml) to give a dark green solid. The solid was then washed with 5 ml of 1N HCl and dried in vacuo. Yield: 68 mg, 0.79 mmol, 56%. $^1$H-NMR(CD$_3$ OD): δ1.56 (m, 4H), 1.73 (m, 4H), 1.94 (m, 4H), 1.98 (m, 2H), 2.04 (s, 12H), 2.34 (m, 4H), 2.75 (m, 4H), 4.3 (m, 4H), 7.5 (m, 2H), 7.65– 8.26 (m, 12H), 8.56 (m, 2H).

2(c). Synthesis of NHMI ylimidazole (20 mg, 0.25 mmol) in 50 µl of DMF was allowed to stand for 7 days. The solvent was then removed under reduced pressure and the residue was dissolved in 200 µl of methylene chloride and 1 ml of ethyl acetate was added to precipitate the product. Yield: 3.2 mg, 0.0034 mmol, 28%.

3. Synthesis of BHDMAP-succinimidyl ester

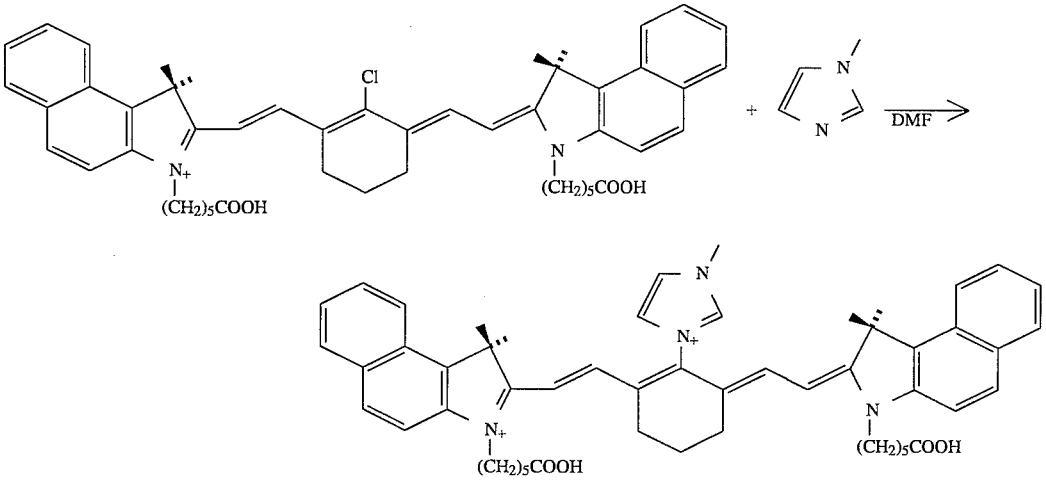

A solution of NHCl (10 mg, 0.012 mmol) and N-meth-

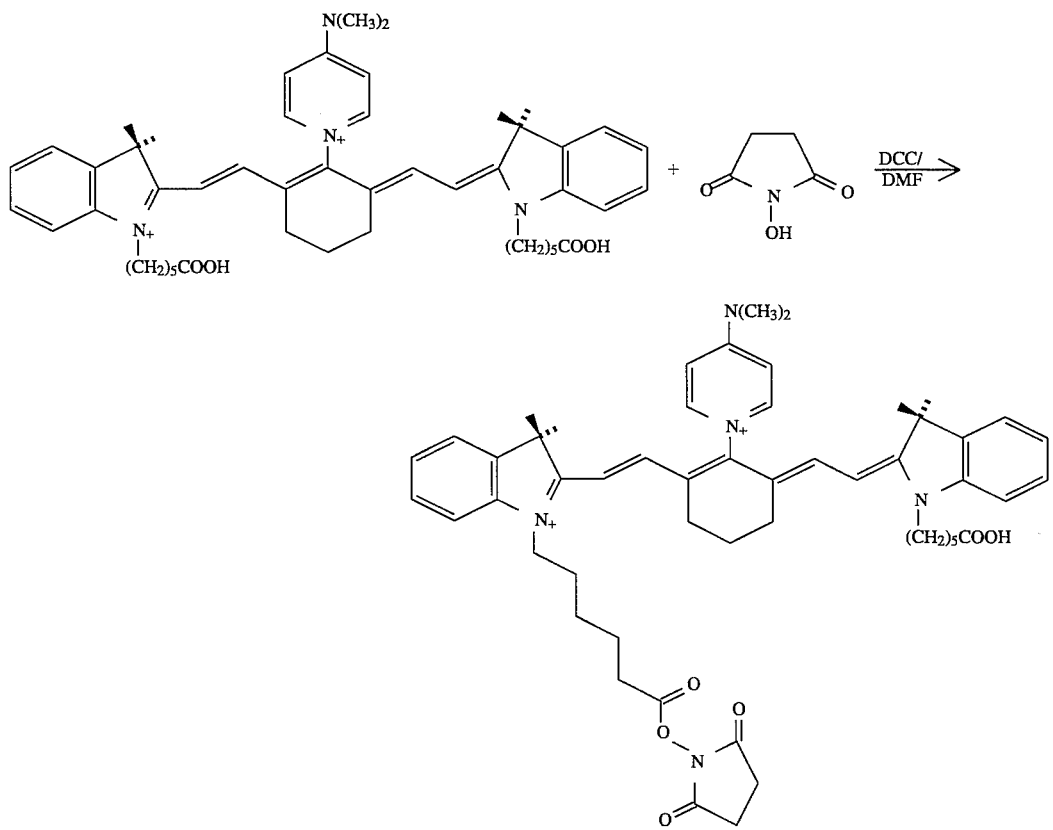

The reaction sequence for the synthesis of BHDMAP-succinimidyl ester is shown above. To a solution of BHDMAP (2 mg, 2 μmol) in DMF was added N-hydroxysuccinimide (3 μg, 19 mmol) and dicyclohexylcarbodiimide (2 mg, 10 μmol). The reaction progress was monitored by HPLC on a POROS R2 column (20% to 40% acetonitrile vs. 0.1M triethylammonium acetate over three min, 5 mL/min). After 6 h the reaction mixture contained starting dye (17%), monoester (60%) and diester (23%). Acetic acid (20 μL) and methanol (0.5 mL) were added and the solution filtered to remove dicyclohexylurea. The solution was concentrated to dryness and redissolved in DMF (0.5 mL). The concentration of the succinimidyl ester solution was determined by dilution of an aliquot into phosphate buffered saline and measurement of the optical density at 786 nm. The extinction coefficient was assumed to be 200,000 $cm^{-1}M^{-1}$. The concentration of BHDMAP succinimidyl ester was found to be 12 mg/mL.

4. Antibody Labeling with BHDMAP

To a solution of mouse IgG (100 μL, 2.5 mg/mL) was added BHDMAP succinimidyl ester (1.3 μL, 12 mg/mL) and bicarbonate buffer (5 μL, 1M, pH 9.2). After 15 min at ambient temperature the excess dye was removed by size exclusion gel filtration. The dye/protein ratio was determined by UV-visible absorbance spectra. The extinction coefficient of the protein was assumed to be 170,000 $cm^{-1}M^{-1}$ at 280 nm. FIG. 1 shows the spectrum of the BHDMAP-protein conjugate.

5. Absorbance Spectra of Dyes in Salt Solution

Figure 3:
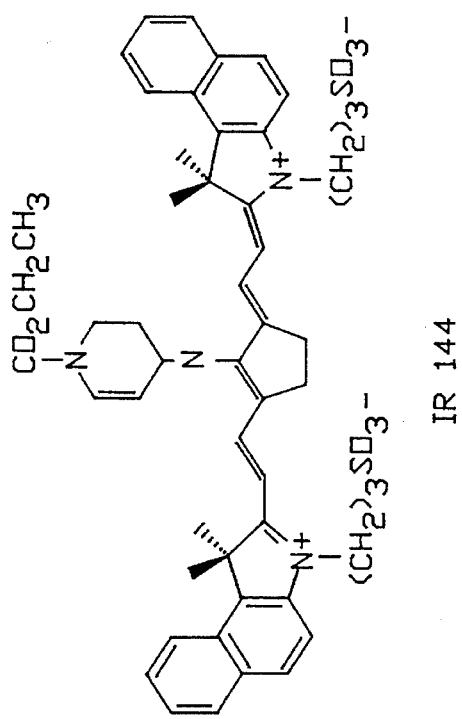
FIG. 3 depicts the spectra of IR144 in a low salt solution (0.1M NaCl, 50 mM phosphate, pH 7) and in dimethylformamide.
Figure 3:
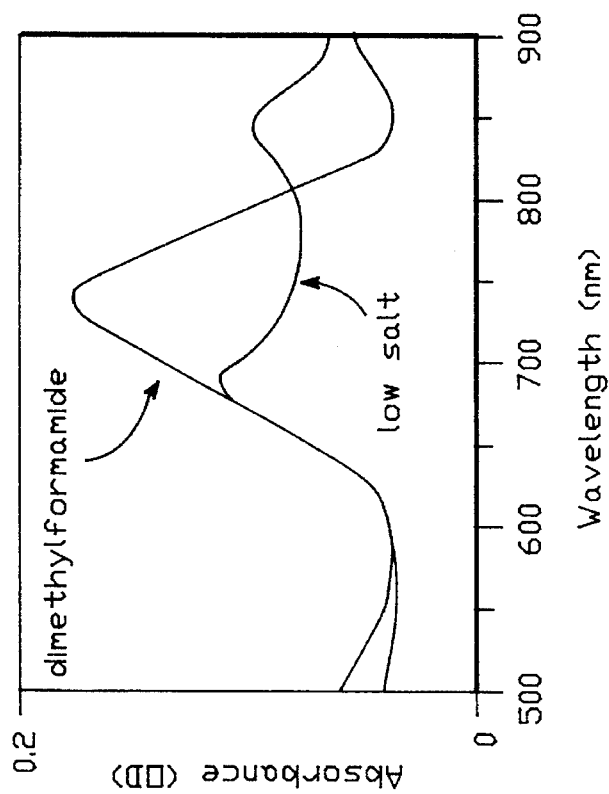

The tendency of dyes to aggregate on proteins can be simulated by measuring the absorbance of the dye in low and high salt solutions. High salt solutions simulate the environment of the dye in high local concentration on the surface of a protein. FIG. 2 shows the spectra of BHCl and BHDMAP in low (0.1M NaCl, 50 mM phosphate, pH 7) and high (3.8M NaCl, 50 mM phosphate, pH 7) salt solutions. BHCl appears to aggregate even in low salt, and in high salt the absorbance maximum has shifted to shorter wavelength. In contrast, the more ionic dye, BHDMAP, shows little aggregation in low and high salt solutions. FIG. 3 shows the spectra of a related dye, IR144, in low salt and in dimethylformamide solutions. Based on the spectra shown in FIG. 3, IR144 appears to aggregate in low salt solutions.

6. Photodecomposition of Dyes

The photostability of several cyanine dyes were compared. Cy5 and Cy7 are the penta- and hepta-methine derivatives, respectively, of a class of arylsulfinate dyes described in U.S. Pat. No. 5,268,486. The structures of BHCl, NHMI and BHDMAP are found in Table 1.

Figure 4:
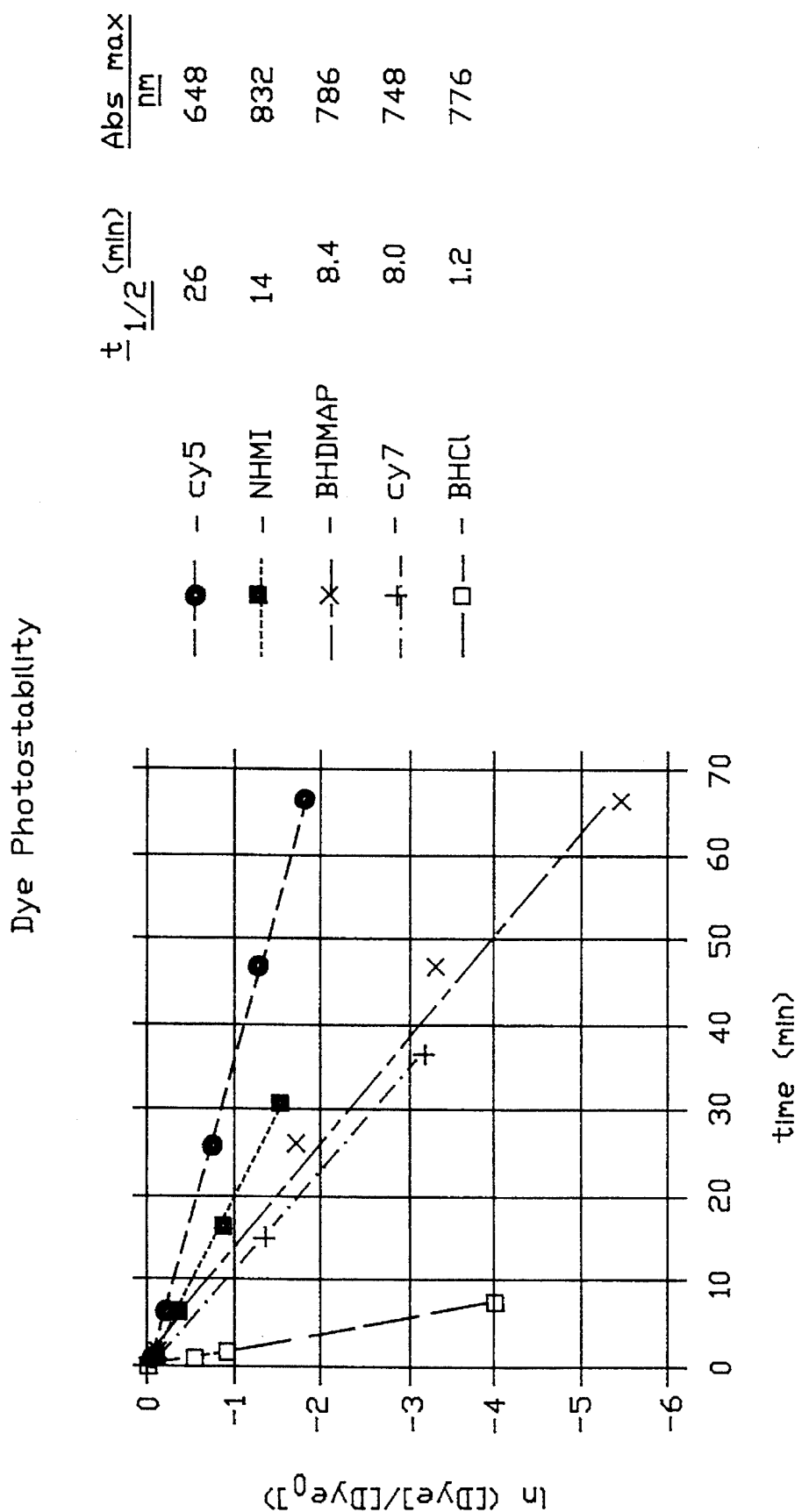
FIG. 4 depicts the photodecomposition rates of several cyanine dyes. Cy5 and Cy7 are arylsulfonate dyes of U.S. Pat. No. 5,268,486.

Solutions of dyes in phosphate buffered saline were irradiated in 1 mL methylacrylate disposable cuvettes with a halogen lamp. The intitial absorbance of each dye varied from 0.5 to 1.7 O.D. units. The absorbance of the dye solutions at the absorbance maxium of each dye was monitored periodically. The concentration of the dye was assumed to be proportional to the optical density of the dye solution in accordance with Beer's Law. A plot of the logarithm of the normalized absorbance (ln[Dye]/[Dye]$_0$) vs. time is shown in FIG. 4. Values of k were determined from least squares analysis and the half-life of each dye determined.

The most stable dye was found to be the dye with the shortest wavelength, Cy5, whose structure contains five methine groups. The remaining dyes contain seven methine groups. BHDMAP, NHMI and Cy7 all have similar stabilities. The least stable dye was found to be BHCl. Substitution of the chloride with dimethylaminopyridine to provide BHDMAP was found to improve the photostability of the cyanine dye seven-fold.

While the present invention is disclosed by reference to the preferred embodiments and examples detailed above, it is to be understood that these examples are intended in an illustrative rather than limiting sense, as it is contemplated that modifications will readily occur to those skilled in the art, which modifications will be within the spirit of the invention and the scope of the appended claims.

What is claimed is:

1. A cyanine dye having the formula

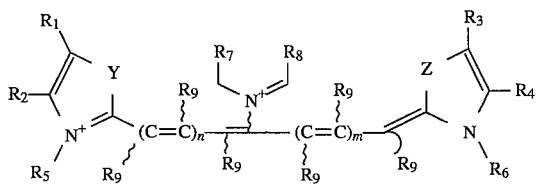

wherein n and m are each independently either 0, 1, 2 or 3;

$R_1$ and $R_2$ are taken together to form an aromatic ring or a fused polycyclic aromatic ring;

$R_3$ and $R_4$ are taken together to form an aromatic ring or a fused polycyclic aromatic ring;

$R_5$ and $R_6$ are independently selected from the group consisting of $(CH_2)_pX$ where p is 1–18 and X is a functional group that reacts with amino, hydroxy or sulfhydryl nucleophiles;

$R_7$ and $R_8$ are independently selected from the group consisting of hydrogen, C1–C10 alkyl groups and where $R_7$ and $R_8$ are taken together to form a five- or six- membered heterocyclic ring;

$R_9$ are each independently selected from the group consisting of hydrogen, alkyl and where more than one $R_9$ are taken together to form a five- or six- membered ring;

Y is selected from the group consisting of $C(CH_3)_2$ and S; and

Z is selected from the group consisting of $C(CH_3)_2$ and S.

2. A cyanine dye according to claim 1 wherein $R_7$ and $R_8$ are taken together to form a ring selected from the group consisting of pyridinium, imidazolium, pyrrolium, pyrazolium, pyrazinium, pyrimidinium, pyridazinium, purinium, quinolinium and isoquinolinium.

3. A cyanine dye according to claim 2 wherein $R_7$ and $R_8$ are taken together to form a pyridinium or imidazolium ring.

4. A cyanine dye according to claim 3 wherein $R_7$ and $R_8$ are taken together to form a substituent selected from the group consisting of: a 4-dimethylaminopyridinium, 4-(4-morpholinyl)-pyridinium, and a 1-methylimidazolium substitutent.

5. A cyanine dye according to claim 1 where X is independently selected from the group consisting of carboxylic acids, acid halides, sulfonic acids, esters, aldehydes, disulfides, isothiocyanates, isocyanates, monochlorotriazine, dichlorotriazine, mono- or di-halogen substituted pyridines, mono- or di-halogen substituted diazines, maleimide, aziridines, sulfonyl halides, hydroxysuccinimide esters, hydroxysulfosuccinimide esters, imido esters, hydrazines, azidonitrophenyl, azides, 3-(2-pyridyl dithio)propionamide and glyoxal.

6. A cyanine dye according to claim 5 where X is a carboxylic acid.

7. A cyanine dye according to claim 5 wherein $R_7$ and $R_8$ are taken together to form a ring selected from the group consisting of pyridinium, imidazolium, pyrrolium, pyrazolium, pyrazinium, pyrimidinium, pyridazinium, purinium, quinolinium and isoquinolinium.

8. A cyanine dye according to claim 1 wherein (n+m) is less than or equal to 3.

9. A cyanine dye according to claim 8 wherein n=1 and m=1.

10. A cyanine dye according to claim 1 wherein Y and Z each are $C(CH_3)_2$.

11. A cyanine dye having the formula

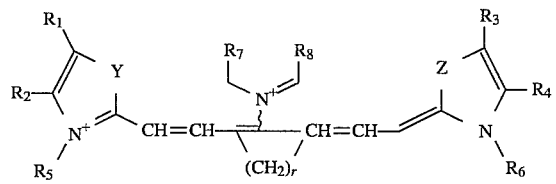

wherein r is 1, 2 or 3;

$R_1$ and $R_2$ are taken together to form an aromatic ring or a fused polycyclic aromatic ring;

$R_3$ and $R_4$ are taken together to form an aromatic ring or a fused polycyclic aromatic ring;

$R_5$ and $R_6$ are independently selected from the group consisting of $(CH_2)_pX$ where p is 1–18 and X is a functional group that reacts with amino, hydroxy or sulfhydryl nucleophiles;

$R_7$ and $R_8$ are independently selected from the group consisting of hydrogen, C1–C10 alkyl and where $R_7$ and $R_8$ are taken together to form a five- or six- membered heterocyclic ring;

Y is selected from the group consisting of $C(CH_3)_2$ and S; and

Z is selected from the group consisting of $C(CH_3)_2$ and S.

12. A cyanine dye according to claim 11 wherein $R_7$ and $R_8$ are taken together to form a ring selected from the group consisting of pyridinium, imidazolium, pyrrolium, pyrazolium, pyrazinium, pyrimidinium, pyridazinium, purinium, quinolinium and isoquinolinium.

13. A cyanine dye according to claim 12 wherein $R_7$ and $R_8$ are taken together to form a pyridinium or imidazolium ring.

14. A cyanine dye according to claim 13 wherein $R_7$ and $R_8$ are taken together to form a substituent selected from the group consisting of: a 4-dimethylaminopyridinium, 4-(4-morpholinyl) pyridinium, and a 1-methylimidazolium substitutent.

15. A cyanine dye according to claim 11 where X is independently selected from the group consisting of carboxylic acids, acid halides, sulfonic acids, esters, aldehydes, disulfides, isothiocyanates, isocyanates, monochlorotriazine, dichlorotriazine, mono- or di-halogen substituted pyridines, mono- or di-halogen substituted diazines, maleimide, aziridines, sulfonyl halides, hydroxysuccinimide esters, hydroxysulfosuccinimide esters, imido esters, hydrazines, azidonitrophenyl, azides, 3-(2-pyridyl dithio)propionamide and glyoxal.

16. A cyanine dye according to claim 15 where X is a carboxylic acid.

17. A cyanine dye according to claim 15 wherein $R_7$ and $R_8$ are taken together to form a ring selected from the group consisting of pyridinium, imidazolium, pyrrolium, pyrazolium, pyrazinium, pyrimidinium, pyridazinium, purinium, quinolinium and isoquinolinium.

18. A cyanine dye according to claim 11 wherein Y and Z each are $C(CH_3)_2$.

19. A cyanine dye selected from the group consisting of:

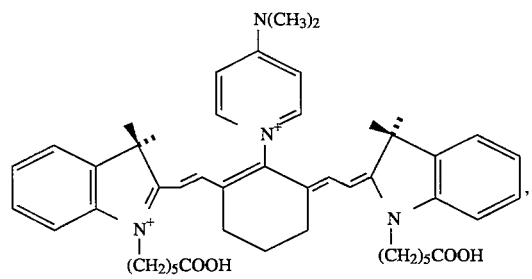
,

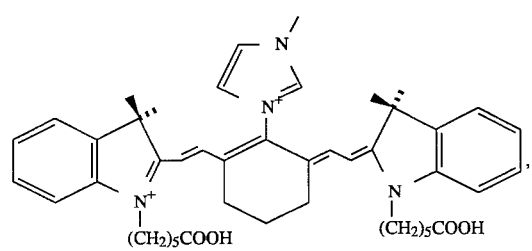
,

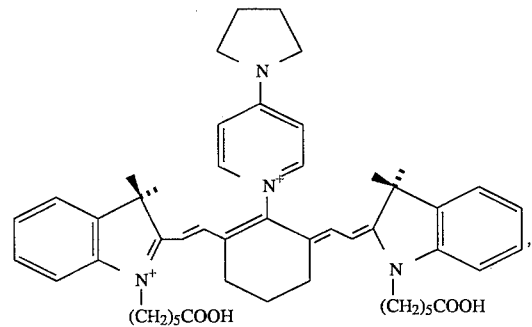
,

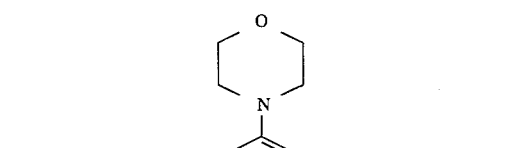

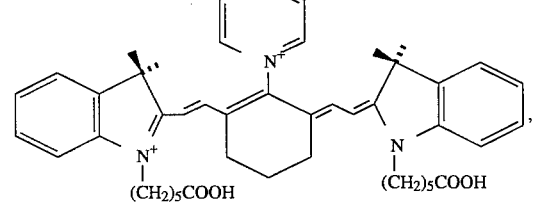
,

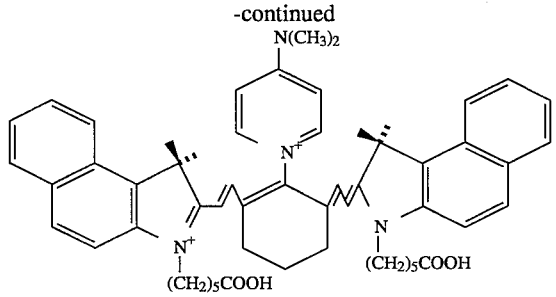
,

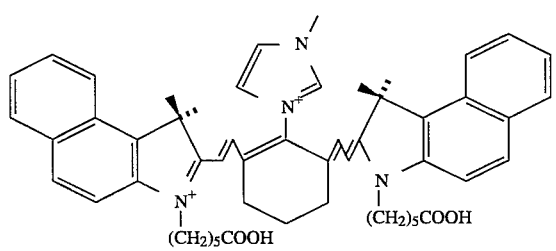
,

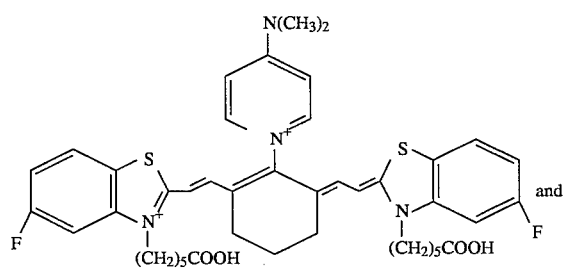
and

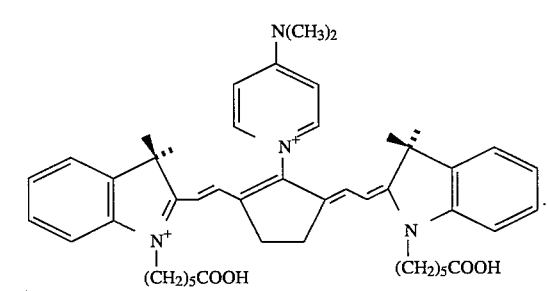
.

20. Method for fluorescent labeling a molecule comprising:
labeling a molecule having an amino, hydroxy or sulfhydryl functional group with a cyanine dye having the formula

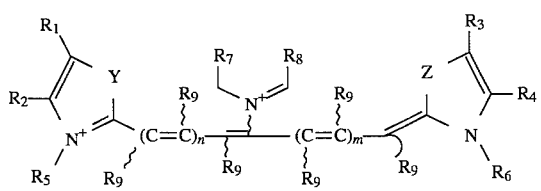

wherein n and m are each independently either 0, 1, 2 or 3;

$R_1$ and $R_2$ are taken together to form an aromatic ring or a fused polycyclic aromatic ring;

$R_3$ and $R_4$ are taken together to form an aromatic ring or a fused polycyclic aromatic ring;

$R_5$ and $R_6$ are independently selected from the group consisting of $(CH_2)_pX$ where p is 1–18 and X is a functional group that reacts with amino, hydroxy or sulfhydryl nucleophiles;

$R_7$ and $R_8$ are independently selected from the group consisting of hydrogen, C1–C10 alkyl and where $R_7$ and $R_8$ are taken together to form a five- or six-membered heterocyclic ring;

$R_9$ are each independently selected from the group consisting of hydrogen, alkyl and where more than one $R_9$ are taken together to form a five- or six- membered ring;

Y is selected from the group consisting of $C(CH_3)_2$ and S; and

Z is selected from the group consisting of $C(CH_3)_2$ and S.

21. A method according to claim 20 wherein the molecule is selected from the group consisting of antibodies, DNA, carbohydrates and cells.

22. A method according to claim 20 wherein $R_7$ and $R_8$ of the cyanine dye are taken together to form a ring selected from the group consisting of pyridinium, imidazolium, pyrrolium, pyrazolium, pyrazinium, pyrimidinium, pyridazinium, purinium, quinolinium and isoquinolinium.

23. A method according to claim 22 wherein $R_7$ and $R_8$ of the cyanine dye are taken together to form a pyridinium or imidazolium ring.

24. A method according to claim 23 wherein $R_7$ and $R_8$ of the cyanine dye are taken together to form a substituent selected from the group consisting of: a 4-dimethylaminopyridinium, 4-(4-morpholinyl) pyridinium, and a 1-methylimidazolium substitutent.

25. A method according to claim 20 wherein (n+m) is less than or equal to 3.

26. A method according to claim 25 wherein n=1 and m=1.

27. A method according to claim 20 wherein Y and Z of the cyanine dye are $C(CH_3)_2$.

28. Method for fluorescent labeling a molecule comprising:

labeling a molecule having an amino, hydroxy or sulfhydryl functional group with a cyanine dye having the formula

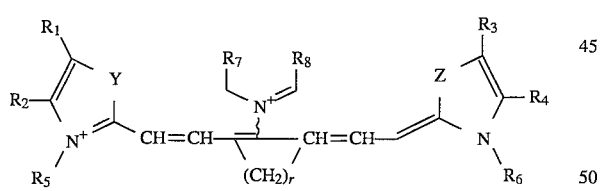

wherein r is 1, 2 or 3;

$R_1$ and $R_2$ are taken together to form an aromatic ring or a fused polycyclic aromatic ring;

$R_3$ and $R_4$ are taken together to form an aromatic ring or a fused polycyclic aromatic ring;

$R_5$ and $R_6$ are independently selected from the group consisting of $(CH_2)_pX$ where p is 1–18 and X is a functional group that reacts with amino, hydroxy or sulfhydryl nucleophiles;

$R_7$ and $R_8$ are independently selected from the group consisting of hydrogen, C1–C10 alkyl and where $R_7$ and $R_8$ are taken together to form a five- or six-membered heterocyclic ring;

Y is selected from the group consisting of $C(CH_3)_2$ and S; and

Z is selected from the group consisting of $C(CH_3)_2$ and S.

29. A method according to claim 28 wherein $R_7$ and $R_8$ are taken together to form a ring selected from the group consisting of pyridinium, imidazolium, pyrrolium, pyrazolium, pyrazinium, pyrimidinium, pyridazinium, purinium, quinolinium and isoquinolinium.

30. A method according to claim 29 wherein $R_7$ and $R_8$ are taken together to form a pyridinium or imidazolium ring.

31. A method according to claim 30 wherein $R_7$ and $R_8$ are taken together to form a substituent selected from the group consisting of: a 4-dimethylaminopyridinium, 4-(4-morpholinyl)pyridinium, and a 1-methylimidazolium substitutent.

32. A method according to claim 28 where X is independently selected from the group consisting of carboxylic acids, acid halides, sulfonic acids, esters, aldehydes, disulfides, isothiocyanates, isocyanates, monochlorotriazine, dichlorotriazine, mono- or di-halogen substituted pyridines, mono- or di-halogen substituted diazines, maleimide, aziridines, sulfonyl halides, hydroxysuccinimide esters, hydroxysulfosuccinimide esters, imido esters, hydrazines, azidonitrophenyl, azides, 3-(2-pyridyl dithio)propionamide and glyoxal.

33. A method according to claim 32 where X is a carboxylic acid.

34. A method according to claim 33 wherein $R_7$ and $R_8$ are taken together to form a ring selected from the group consisting of pyridinium, imidazolium, pyrrolium, pyrazolium, pyrazinium, pyrimidinium, pyridazinium, purinium, quinolinium and isoquinolinium.

35. A method according to claim 28 wherein Y and Z each are $C(CH_3)_2$.

36. Method for fluorescent labeling a molecule comprising:

labeling a molecule having an amino, hydroxy or sulfhydryl functional group with a cyanine dye selected from the group consisting of:

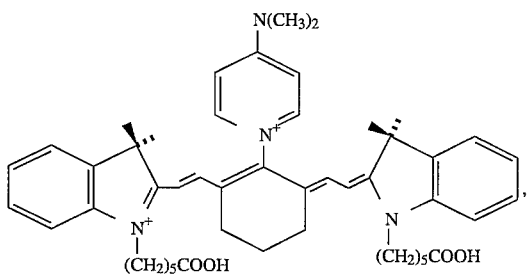

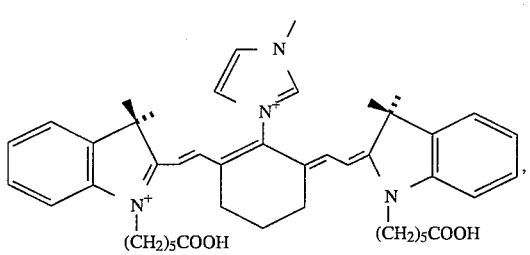

25
-continued
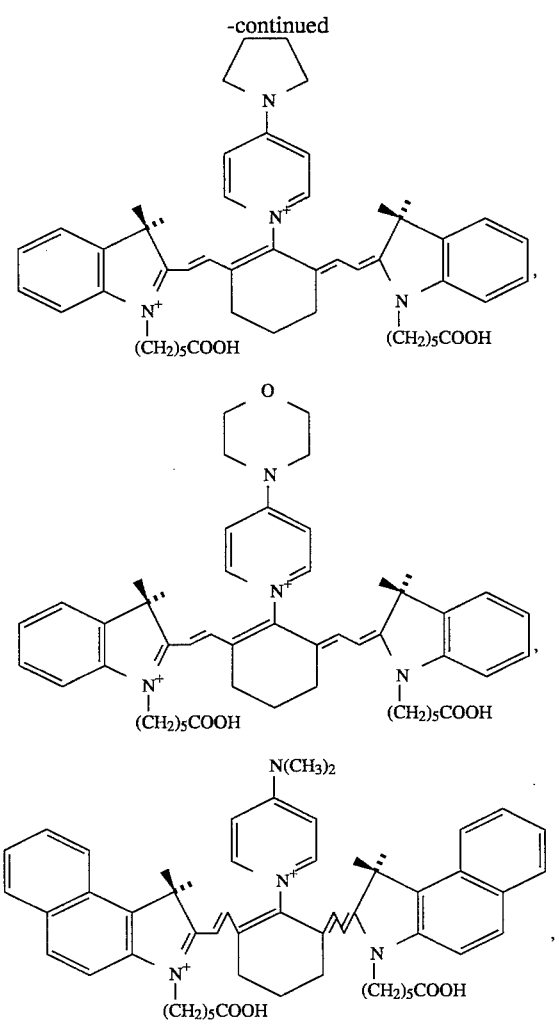
26
-continued
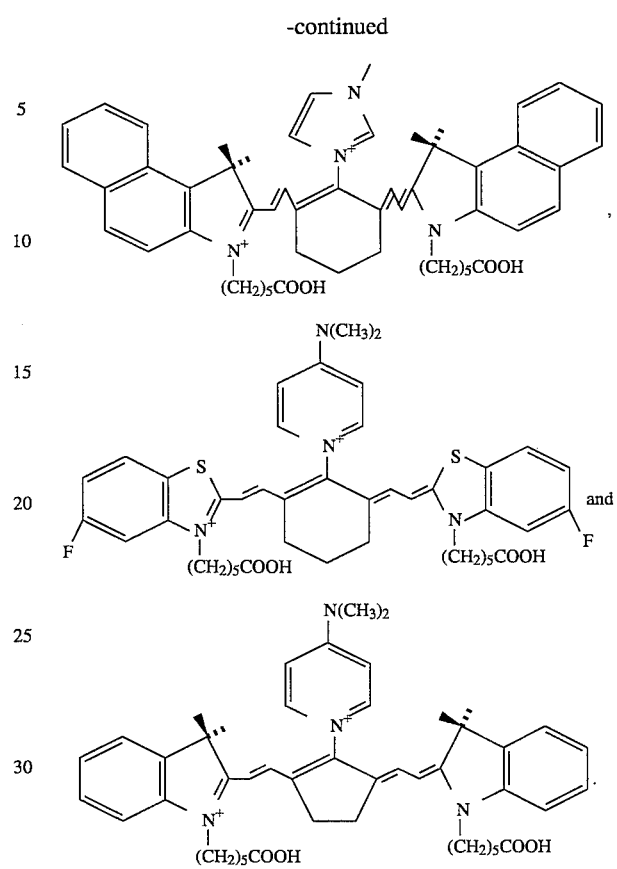
and
* * * * *